United States Patent
Sommer (10) Patent No.: US 7,283,607 B2
(45) Date of Patent: Oct. 16, 2007

(54) CONTINUOUSLY OPERATING TOMOGRAPHY APPARATUS AND METHOD FOR THE OPERATION THEREOF

(75) Inventor: Andres Sommer, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 106 days.

(21) Appl. No.: 10/542,497

(22) PCT Filed: Dec. 8, 2003

(86) PCT No.: PCT/DE03/04032

§ 371 (c)(1),
(2), (4) Date: Dec. 30, 2005

(87) PCT Pub. No.: WO2004/066841

PCT Pub. Date: Aug. 12, 2004

(65) Prior Publication Data

US 2006/0140333 A1    Jun. 29, 2006

(30) Foreign Application Priority Data

Jan. 17, 2003 (DE) .................. 103 01 891

(51) Int. Cl.
*H05G 1/60* (2006.01)
*H05G 1/02* (2006.01)

(52) U.S. Cl. .................... 378/15; 378/50; 378/196; 378/197; 378/199

(58) Field of Classification Search .......... 378/15, 378/20, 57, 196, 197
See application file for complete search history.

(56) References Cited

U.S. PATENT DOCUMENTS

| | | | |
|---|---|---|---|
| 5,093,850 A | 3/1992 | Dinwiddie et al. | 378/15 |
| 5,247,556 A | 9/1993 | Eckert et al. | 378/4 |
| 5,594,772 A | 1/1997 | Toki et al. | 378/114 |
| 5,761,269 A | 6/1998 | Sugihara et al. | 378/199 |
| 5,901,198 A * | 5/1999 | Crawford et al. | 378/57 |
| 6,198,790 B1 | 3/2001 | Pflaum | 378/9 |
| 6,292,527 B1 | 9/2001 | Guendel | 378/15 |
| 6,412,979 B1 | 7/2002 | Hell et al. | 378/200 |
| 6,480,561 B1 | 11/2002 | Proksa | 378/16 |
| 6,507,639 B1 | 1/2003 | Popescu | 378/108 |
| 6,709,156 B1 | 3/2004 | Hell et al. | 378/199 |
| 6,988,827 B2 * | 1/2006 | Mueller | 378/199 |

FOREIGN PATENT DOCUMENTS

| | | |
|---|---|---|
| EP | 0 024 325 A1 | 3/1981 |
| EP | 0 531 993 B1 | 1/1998 |

* cited by examiner

*Primary Examiner*—Allen C. Ho
(74) *Attorney, Agent, or Firm*—Schiff Hardin LLP (57) ABSTRACT

In a continuously operating tomography apparatus and an operating method therefore, a scanner unit is rotated around a system axis and first and second examination subjects are successively moved into the scanner unit and respective examinations of the first and second examination subjects are conducted without interruption of rotation of the scanner unit. The rotation frequency of the scanning unit is set differently dependent on the type of examination to be conducted, and when no examination of an examination subject is taking place, the scanning unit is rotated at a predetermined rest rotation frequency, that is smaller than a smallest of the available rotation frequencies for the examinations, or is an average of the rotation frequencies available for the examinations.

15 Claims, 4 Drawing Sheets

CONTINUOUSLY OPERATING TOMOGRAPHY APPARATUS AND METHOD FOR THE OPERATION THEREOF

BACKGROUND OF THE INVENTION

1. Field of the Invention

The present invention relates to imaging tomography apparatuses, in particular for medical examinations, in particular in the fields of x-ray computed tomography (CT), single photon emission tomography (SPECT) and positron emission tomography (PET).

The invention also concerns a method for operation of a tomography apparatus of the type having a scanning unit that can rotate around a system axis and a bearing device for an examination subject.

The invention also concerns a tomography apparatus with a scanning unit that can be rotated around a system axis, a control device for activation of the scanning unit and a bearing device for an examination subject.

2. Description of the Prior Art

The conventional implementation of examinations of a number of examination subjects or patients by means of an x-ray computed tomography apparatus is as follows:

1. generation of an x-ray shadow image (topogram, scanogram, scout view) with a non-rotating x-ray source, with a first examination subject moved on the bearing device relative to x-ray source and detector system in the direction of the system axis,
2. definition of the region (scan region) of the first examination subject to be acquired in the direction of the system axis in the actual examination on the basis of the generated x-ray shadow image,
3. positioning of the first examination subject by moving the bearing device to the start point of the scan region,
4. start of the rotation of the x-ray source around the system axis,
5. implementation of the actual examination of the first examination subject in the form of a slice and/or volume scan with a rotating x-ray source, for the most part in the form of a spiral scan,
6. interruption of the rotation of the x-ray source and
7. repetition of the steps 1-6 with the next examination subject.

Among other things, the topogram should allow minimization of the radiation dose by avoiding unnecessary, projection data from being acquired (for example in the spiral scan). Thus the topogram covers a larger region than would then be actually necessary for the subsequent image reconstruction in the desired region. Moreover, the topogram serves as the documentation of the scanned region.

This conventional method has disadvantages:

a) The entire workflow proves to be relatively long, which is undesirable for efficiency reasons and for medical reasons, in particular when the subject is an emergency patient.
b) If x-ray shadow images are desired from various projection directions (viewing angles), for example "from the front" and "from the side", the patient is moved three times with the bed, namely twice for generation of the shadow images and a third time for the spiral scan.

For optimization of the workflow and the flexibility, so-called "growing topograms" have been proposed, whereby an x-ray shadow image is acquired and displayed simultaneously or inline with the spiral scan, the x-ray shadow image growing with the spiral scan. Such a procedure is described in DE 198 02 405 A1 for a computed tomography apparatus with a 2-tube system. Computed tomography apparatuses with only one x-ray radiator have also been proposed in which the topogram likewise exists quasi-"online" by extraction of data that accrue during the actual scanning from a number of directions, for example in the spiral scan. Such methods are known from EP 0 531 993 B1, DE 41 03 588 C1 and DE 199 25 395 A1.

From the cited documents it is also known to allow one or two x-ray tubes to emit radiation only in a pulsed fashion at the projection angle or angles necessary for a tomogram.

Moreover, in EP 1 116 475 A1 a synthetic topogram is proposed that is generated by, initially, a 3D data set being reconstructed from the projection data sets and the shadow image being subsequently calculated from the 3D data set.

SUMMARY OF THE INVENTION

An object of the present invention is to provide a method as well as a tomography apparatus of the type described above that allow the entire workflow to be executed more quickly in the examination of a number of patients.

According to the invention, this object is achieved by a method for operation of a tomography apparatus that has a scanning unit that is rotatable around a system axis, a bearing device for an examination subject and a control device for activation of the scanning unit, wherein the rotation of the scanning unit is not interrupted from the beginning of the examination of a first examination subject until the end of the examination of a second examination subject. The rotation frequency of the scanning unit is set differently dependent on the type of the desired examination, for example for an examination of the heart or of the abdomen of a patient. When no examination of an examination subject occurs, a preset rest rotation frequency is set that is smaller than the rotation frequency available for the various examinations or lies in the range of the average value of the rotation frequencies available for the various examinations.

Downtimes arise, for example, before the beginning of the slice and/or volume scanning of the examination subject, to allow the rotation of the scanning unit to be started up and, after the end of the scanning, when the rotation is interrupted until the examination of the next examination subject. The invention prevents such downtimes by continuous rotation of the scanning unit. In particular the scanning unit rotates during the change from one examination subject to the next examination subject.

In addition to accelerating the entire workflow in the examination of a number of patients, the following advantages result with the method according to the invention:

i) The control of the tomography apparatus can be significantly simplified. In particular the repositioning (scanning unit with regard to bearing device, horizontal and vertical) that has been conventionally necessary before each new examination can be omitted, or is at least significantly simplified. The electrical activation of the rotation-driving motors is also simplified.
ii) The measurement times are also reduced by the permanent rotation, which above all is significant when the tomography apparatus is used for emergency patients, when every second counts. Here the advantages are obvious, even when only 1-2 minutes can be saved.
iii) The load for the bearing components of the tomography apparatus is reduced. The lubrication of bearings is also improved by the evened-out movement.

iv) The temperature stability and homogeneity of the entire tomography apparatus is improved. This particularly has an effect in the data acquisition system. The cooling is also thereby simplified.

The interruption-free rotation of the scanning unit can mean a rotation with constant speed, but as previously noted the rotation speed or the rotation frequency preferably set differently dependent on the type of the desired examination (application), for example for an examination of the heart or of the abdomen of a patient.

As noted, the tomography apparatus is controlled such that, in the event that no examination immediately occurs, the scanning unit then rotates with a preset rotation speed ("standby setting"). This rotation speed (rest rotation speed) is, for example, smaller than the rotation speeds available for examinations or lies in the range of the average value of the rotation speeds available for examinations, such that the change of the rotation speed given a new examination is on average small.

Preferably, the rotation speed is continuously changed between the different examinations or between an examination and the rotation in standby setting.

According to a preferred embodiment of the method, the time span of the uninterrupted rotation of the scanning unit extends over a work shift, over a working day or over a number of examinations. The shift or the working day, for example, may depend on the medical establishment with which the tomography apparatus is associated. The time span of the uninterrupted rotation can also extend over a week or longer.

According to a preferred embodiment of the method, the time span of the uninterrupted rotation of the scanning unit extends over at least one hour or over at least three hours.

With regard to particularly long time spans of the uninterrupted rotation, it is advantageous to calibrate the tomography apparatus (in particular to make a position and/or reception channel correction) during the rotation of the scanning unit. The invention is based on the recognition that such a procedure consequently has significantly fewer inaccuracies than is the case for calibration in the downtime and subsequent testing upon rotation. A continuously-rotating measurement system also has the advantage that mechanical inaccuracies produced due to centrifugal forces, for example a deflection of the measurement system, carry significantly less weight, in particular when these are equally taken into account in the calibration.

In a further embodiment, the tomography apparatus is an x-ray computed tomography (CT) apparatus having a scanning unit with an x-ray source that can be rotated around the system axis and a detector system for acquisition of the x-ray radiation emanating from the x-ray source, wherein at least the rotation of the x-ray source—and optionally also that of the detector system—is not interrupted from the beginning of the examination of a first examination subject to the end of the examination of a second examination subject.

Conventionally, the necessity of interrupting the rotation was to acquire a topogram for the previously explained reasons. In accordance with the invention no interruption of the rotation of the scanning unit is necessary for a topogram, even in if it must be completely finished before the actual CT scanning examination subject. This occurs in the following three preferred embodiments:

1) The examination of the first and/or second examination subject includes the following steps:
   a) acquisition of an x-ray shadow image of the examination subject given rotating x-ray source, and then:
   b) implementation of a slice and/or volume scanning of the examination subject with a rotating x-ray source, whereby the x-ray source emits x-ray radiation at a plurality of angle positions and respective projection data are detected by the detector system, and wherein the rotation of the x-ray source is not interrupted from the beginning of the step a) to the end of the step b).

In spite of uninterrupted rotation, a topogram can be generated that is concluded before the actual CT examination (step b).

The x-ray source thereby in particular respectively emits x-ray radiation in a pulsed manner at an angle position that can be predetermined for the x-ray shadow image for acquisition of the x-ray shadow image in step a), and corresponding radiographic data are detected by the detector system. The x-ray source can simultaneously be moved parallel to the system axis and relative to the examination subject. This relative movement can possibly be omitted given a corresponding detector system expanded in the direction of the system axis.

2) The examination of the first and/or second examination subject includes the following steps:
   a) implementation of a slice and/or volume scanning of the examination subject with a rotating x-ray source, whereby the x-ray source emits x-ray radiation at a plurality of angle positions and respective projection data are detected by the detector system, and wherein the x-ray source is moved parallel to the system axis and relative to the examination subject;
   b) generation of an x-ray shadow image of the examination subject simultaneously with the slice and/or volume scanning, with matching projection data being selected for the x-ray shadow image from the data accumulating in the slice and/or volume scanning.

With uninterrupted rotation, a mutually growing topogram can thereby be generated. If the detector system extends sufficiently in the direction of the system axis, the relative movement of the x-ray source parallel to the system axis can possibly be omitted.

3) The examination of the first and/or second examination subject includes the following method steps:
   a) implementation of a slice and/or volume scanning of the examination subject with a rotating x-ray source, whereby the x-ray source emits x-ray radiation at a number of angle positions and respective projection data are detected by the detector system, and the x-ray source is moved parallel to the system axis and relative to the examination subject;
   b) reconstruction of a 3D data set from the projection data accumulating in the slice and/or volume scan;
   c) calculation from the 3D data set of an x-ray shadow image of the examination subject as a synthetic projection image.

A synthetic topogram can be generated with uninterrupted rotation. Given a corresponding detector system extended in the direction of the system axis, the relative movement of the x-ray source parallel to the system axis can possibly be omitted.

In the method according to the invention, the slice and/or volume scan can ensue in the form of a spiral scan according to a particularly preferred embodiment. For this, the bearing device on the one hand and the x-ray source and the detector system can be movable relative to one another, substantially in the direction of the system axis, during displacement of the x-ray source around the system axis.

The above object also is achieved according to the invention by a tomography apparatus with a scanning unit that can rotate around a system axis, a bearing device for an examination subject and a control device for activation of the scanning unit, wherein the control device causes the scanning unit to rotate without interruption from the beginning of the examination of a first examination subject until the end of the examination of a second examination subject. The rotation frequency of the scanning unit can be set differently by the control device dependent on the type of the desired examination, for example for an examination of the heart or of the abdomen of a patient. When no examination of an examination subject occurs, a preset rest rotation frequency is set that is smaller than the rotation frequency available for the various examinations or lies in the range of the average value of the rotation frequencies available for the various examinations.

Advantages and preferred embodiments of the tomography apparatus according to the invention are analogous to those for the method of the invention.

The tomography apparatus according to the invention is preferably fashioned as an x-ray computed tomography (CT) apparatus. It can also be fashioned as a single photon emission tomography (SPECT) apparatus or as a positron emission tomography (PET) apparatus or as a combination of such apparatuses, for example as a PET/CT apparatus. The method according to the invention is also applicable for such apparatuses.

According to a preferred exemplary embodiment, the scanning unit has an x-ray source that can be rotated around a system axis and a detector system for acquisition of the x-ray radiation emanating from the x-ray source, and the control device causes at least the x-ray source—and optionally also the detector system—to be rotated without interruption from the beginning of the examination of a first examination subject until the end of the examination of a second examination subject.

The tomography apparatus is also preferably is designed for a continuous operation with regard to the electrical power supply to the x-ray generator and/or with regard to the heat dissipation, in particular the cooling of the rotating scanning unit.

For this purpose, the cooling device preferably has, for example, air drivers for generation of an air flow, with the air drivers mounted on a rotating frame that support the scanning unit and dimensioned such that a cooling capacity sufficient to cool the scanning unit is achieved upon rotation of the rotating frame. Special ventilators that must be driven electrically thus can be omitted. This idea is also advantageously applicable in a tomography apparatus that does not rotate continuously.

The air drivers can be fashioned as air scoops that can be mounted inside the rotating frame, for example acting in an annular current channel, or preferably on an outside of the rotating frame or on an outside of a housing wall of the rotating frame.

DESCRIPTION OF THE PREFERRED EMBODIMENTS

Figure 1:
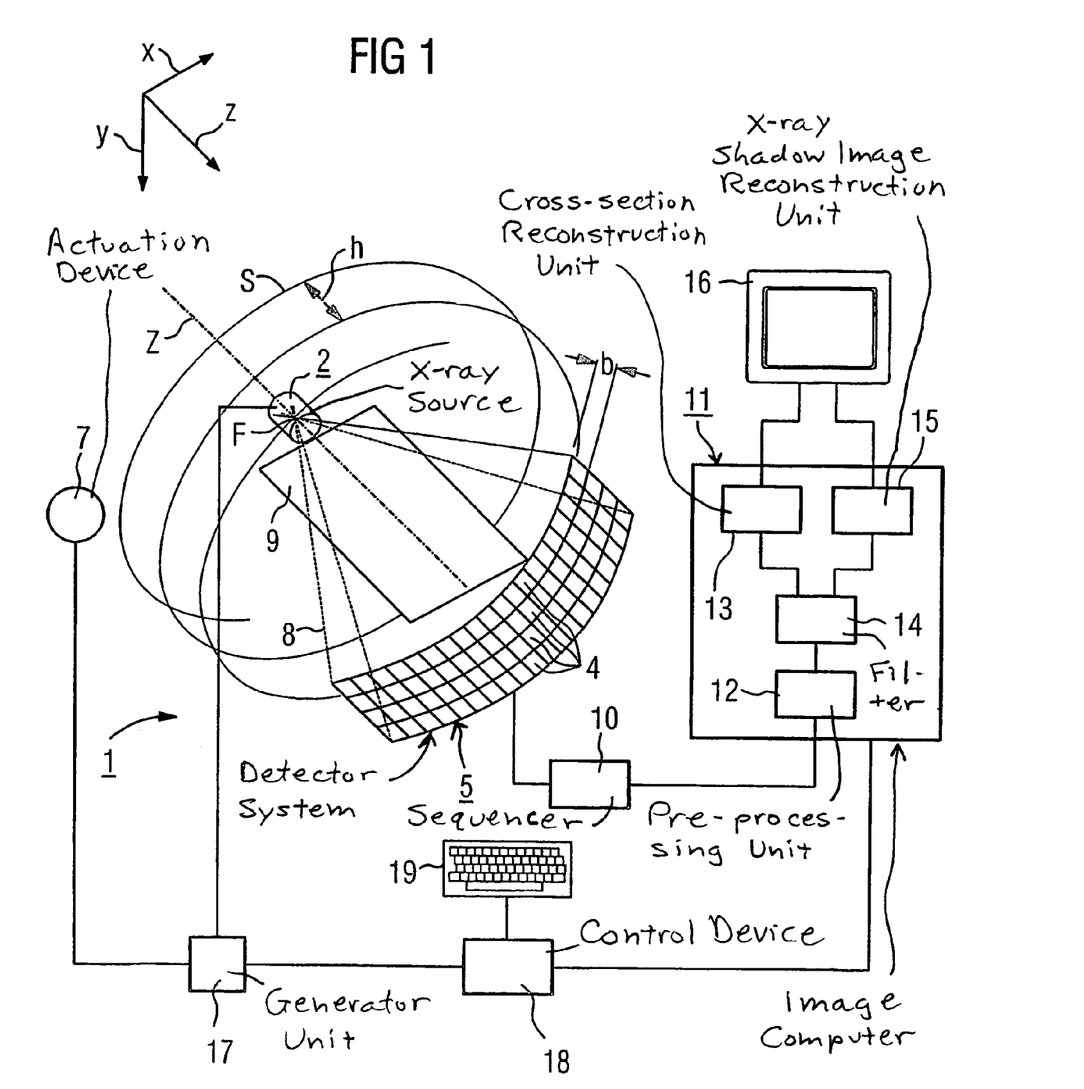
FIG. 1 is a block diagram of a CT apparatus suitable for implementation of the inventive method.

A CT apparatus of the 3rd generation suitable for implementation of the inventive method is shown in FIG. 1 but without, among other things, a housing frame. The scanning unit or measurement of the CT apparatus (designated overall with 1) has an x-ray source 2 and a detector system 5 fashioned as a laminar array of a number of rows and columns of detector elements 4. The x-ray source 2 and the detector system 5 are mounted opposite one another on a rotating frame (not shown), such that a pyramidal x-ray beam with edge rays 8, emanating (in the operation of the CT apparatus) from the x-ray source 2 and gated by adjustable ray diaphragms, strikes on the detector system 5.

The rotating frame (gantry) can be displaced in rotation around a system axis Z by means of the actuation device 7 fashioned as a synchronous motor or alternatively as an asynchronous motor with a belt drive. The system axis Z runs parallel to the z-axis of a spatially-rectangular coordinate system shown in FIG. 1.

The columns of the detector system 5 likewise run in the direction of the z-axis while the rows (whose width b is measured in the direction of the z-axis and is, for example, 1 mm) run transverse to the system axis Z and the z-axis.

In order to be able to bring an examination subject (for example a patient) into the beam path of the x-ray beam, a bearing device 9 is provided that can be moved parallel to the system axis Z, thus in the direction of the z-axis with a synchronization between the rotation movement of the rotating frame and the translation movement of the bearing device 9 in the sense that the ratio of translation speed to rotation speed is constant. This ratio can be adjusted by a desired value for the feed h of the bearing device 9 per rotation of the rotating frame being selected.

A volume of an examination subject located on the bearing device 9 thus can be examined in the course of a volume scan, the volume scan being effected in the form of a spiral scan in the sense that a number of projections be acquired from various projection directions with simultaneous rotation of the scanning unit 1 and translation of the bearing device 9 with the set ratio by means of the scanning unit 1 per revolution of the scanning unit 1. In the spiral scan, the focus F of the x-ray source moves on a spiral path S relative to the bearing device 9.

The measurement data are read out in parallel from the detector elements 4 of each row of the detector system 5 during the spiral scan and, corresponding to the individual projections, are serialized in a sequencer 10 and transferred to an image computer 11.

After pre-processing of the measurement data in a pre-processing unit 12 of the image computer 11, the resulting data stream arrives at a cross-section reconstruction unit 13 that reconstructs from the measurement data slice images of desired slices of the examination subject according to a known method (for example 180LI or 360LI interpolation).

In order to be able to determine the position of the slice (for which a cross-section should be reconstructed) in the z-direction, an x-ray shadow image can also be reconstructed in addition to cross-sections. For this, the portion of the measurement data necessary for reconstruction of an x-ray shadow image is extracted from the data stream coming from the sequencer 10 by a filter 14, and before the data stream arrives at the cross-section reconstruction unit 13. This data portion is supplied to an x-ray shadow image reconstruction unit 15 that reconstructs an x-ray shadow image from the extracted measurement data according to a known method.

The section or x-ray shadow images reconstructed respectively by the cross-section reconstruction unit 13 and the x-ray shadow image reconstruction unit 15 during the implementation of the spiral scan are shown parallel to and synchronous with the spiral scan on a display unit 16 (for example a video monitor) connected to the image computer 11.

The x-ray source 2, for example an x-ray tube, is supplied with the necessary voltages and currents by a generator unit 17. In order to be able to adjust these to the respectively necessary values, a control device 18 with keyboard 19 is associated with the generator unit 17, which control device 18 allows the necessary adjustments. The generator unit 17 also allows an intermittent or pulse-like emission of x-rays at predeterminable angle positions of the x-ray source 2. The angle positions (projection directions) are generated by a position sensor with an encoder.

The further operation and control of the CT apparatus ensue via the control device 18 and the keyboard 19, which is illustrated by the control device 18 is connected with the image computer 11. The control device 18, moreover, serves for the activation of the drive device 7.

The design of the image computer 11 has been described above based on hardware components, namely the pre-processing unit 12, the cross-section reconstruction unit 13, the filter 14 and the x-ray shadow image reconstruction unit 15. Normally, however, the cited components are realized by software modules that run on a universal computer provided with the necessary interfaces. The universal computer can also (deviating from FIG. 1) assume the function of the control device 18.

The generator unit 17 and the drive device 7 allow the following operating modes to be set by the control unit 18:

V: continuous operation of the x-ray source 2 in volume scanning, for example spiral scanning, with an x-ray power parameterized for the generation of slice images, T': continuous operation of x-ray source 2 in spiral scanning with an x-ray power parameterized for the generation of x-ray shadow images (topogram) and reduced relative to the operating mode "V", T: activated operation of the x-ray source 2, whereby the x-ray source 2 radiates an x-ray pulse with the x-ray power parameterized for the generation of x-ray shadow images only when the rotating x-ray source 2 is located in a position corresponding to the desired projection direction for he x-ray shadow image (topogram), and A: disconnected operation, in which the x-ray source 2 does in fact rotate with constant rotation frequency $f_A$ (>0, for example 1 rotation/s) ("standby mode") but is not activated.

Figure 2:
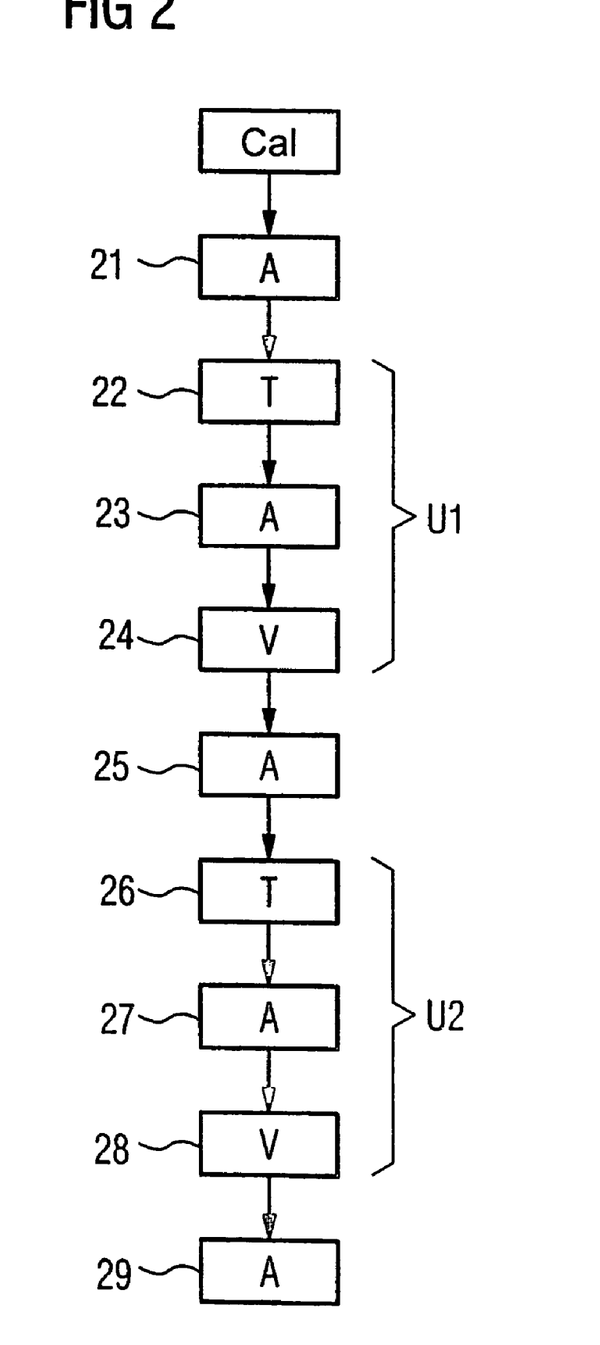
FIG. 2 is a block diagram illustrating an exemplary embodiment of the inventive method.
Figure 3:
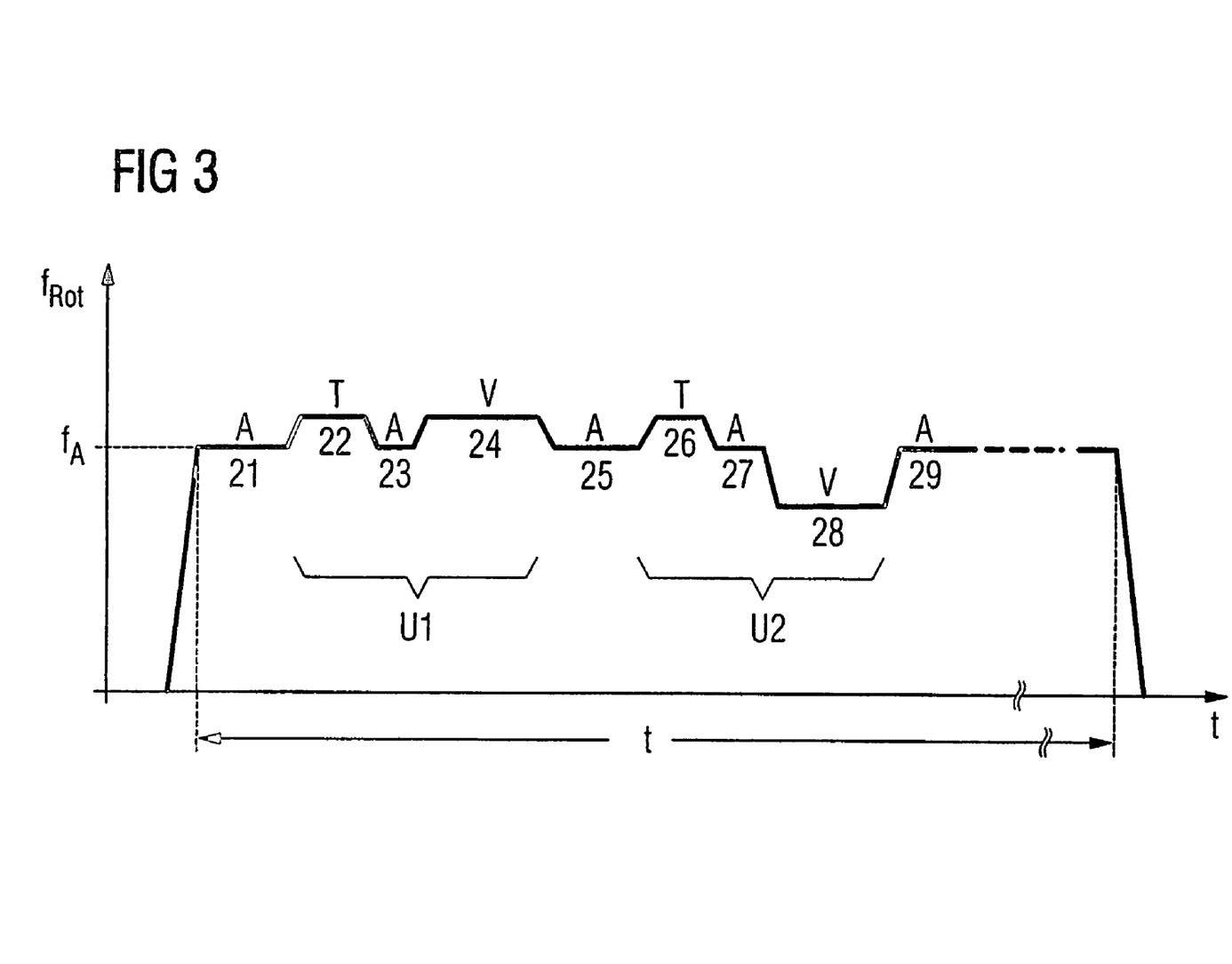
FIG. 3 is a time curve of the rotation speed of a scanning unit of the CT apparatus of FIG. 1 in the exemplary embodiment of FIG. 2.

FIGS. 2 and 3 shows a simplified flowchart or time diagram of the workflow in the examination of a number of examination subjects U1, U2, etc. (The examination subjects as such are not shown) FIG. 2 schematically shows the curve of the rotation frequency $f_{Rot}$ with the time t during the workflow. The t-axis is not scaled linearly: generally a spiral scan will take longer, in comparison with a topogram acquisition, than as shown here.

A calibration step "Cal" is executed at the beginning of a workday or a work week. The control device 18 subsequently brings the scanning unit 1 into rotation in a first park or standby phase 21 with the operating mode "A" in which the CT apparatus remains available until a first examination subject U1 for examination. In the operating step "T", the examination is then begun with a topogram step 22 without interruption of the rotation. Only an x-ray shadow image (topogram) of the first examination subject U1—or alternatively two shadow images laterally and a.p. are reconstructed and displayed. Without interruption of the rotation, in a further standby phase 23 the apparatus is subsequently switched again into the operating mode "A" during which the operating personnel initially establishes a diagnostically-relevant scan region and then, using this, positions the first examination subject U1 at the beginning of the desired scan region. After the positioning has occurred, a spiral scan is implemented with continuous rotation in the operating mode "v" in a volume scan step 24 with rotation speed negligibly increased relative to step 23. When the prior established end of the scan region is reached, without interruption of the rotation the scanning unit 1 is switched again into the operating mode "A" in a further standby phase 25 and the radiation is deactivated, but the scanning unit 1 still rotates. The CT apparatus remains in this state until a further patient should be examined.

The procedure is subsequently repeated as needed with a second examination subject U2, but in the example a different region of the patient is to be examined (different application):

topogram step 26, standby phase 27 with positioning of the second examination subject U2 for the subsequently volume scan 28 with a rotation frequency less—due to the different application—in comparison to the examination of the first examination subject U1, standby phase 29.

The cycles are subsequently repeated again with further examination subjects, with the scanning unit 1 rotating without interruption over a time span Δt of a plurality of hours. The scanning unit 1 can also rotate during the calibration step Cal, which is different than shown in FIGS. 2 and 3.

As an alternative to the operating mode "T", at the beginning of the examination parallel x-ray shadow image reconstruction and cross-section image reconstruction can be implemented in the operating mode "T'". The results are shown in parallel on the display unit 16. Due to the reduced x-ray power, however, the cross-sections can be diagnostically used only in a limited manner.

In the implementations described with FIGS. 2 and 3, it was assumed that the topogram is completely concluded before the actual volume scan, and that both beginning and end of the diagnostically-relevant scan region are thus known. As an alternative, the topogram can be generated only in part before the volume scan is begun: namely, if diagnostically-relevant structures are reached in the operating mode "T'" or "T" with increasing z-feed of the scanning unit 1, the scanning unit 1 can be switched to the operating mode "V" without interruption of the rotation, in which operating mode "V" measurement data are now acquired that (due to the now-higher x-ray power) enable reconstruction of slice images of higher quality that are simultaneously displayed with the x-ray shadow image. After the diagnostically-relevant region has been scanned, in this alternative the scanning unit 1 is switched again into the operating mode "A" in a further standby phase 25 without interruption of the rotation of the scanning unit 1 and the radiation is deactivated, but the scanning unit 1 still rotates further.

In a further alternative operating mode that is particularly of importance for CT apparatuses having a detector system 5 that exhibits a large width in the direction of the system axis Z and thus has a large number of rows, a relative movement between the scanning unit 1 and the bearing device 9 in the direction of the system axis Z (a spiral scan) can be foregone if the extent of the detector system 5 is sufficient to acquire the entire region to be examined. For the case that the extent of the detector system 5 in the direction of the system axis Z is greater than the corresponding extent of the region to be examined, it is sufficient to activate only those rows the detector system 5 that are necessary for acquisition of the examined region.

Conventionally, the rotation operation of the rotating mass in an x-ray computed tomography (CT) apparatus would have to fulfill two criteria:

1. a precise adjustment of the rotation frequency according to specification and
2. a positioning of the mass at a specific angle position for balancing.

In terms of regulation technology, both requirements are very difficult to fulfill together, so that in the past the rotation speed regulation, which is decisive for the imaging in a spiral scan, would often have to take precedence. With only a simple mass positioning method, a number of attempts (for example by braking the mass with a correction angle and studying the braking path), and therewith more time, could be necessary in order to achieve the goal. In the individual case, the angle precision would amount to only approximately +/−5°.

Advantages of the continuous rotation are now that

A) only a constant rotation speed must still be regulated, i.e. the regulation system can be executed comparably simply and the actuator can be reduced, for example, to a very inexpensive asynchronous motor, and that
B) the precision of the angle adjustment for a topogram is significantly higher, thus the subdivision of an angle of the rotation position transmitter (and therewith the result of the generated overview image) is more precise.

A continuously-rotating measurement system also achieves a uniform temperature distribution and thereby allows an increased measurement precision, thus a better image quality. A continuously-rotating measurement system prevents "temperature peaks", i.e. locally pronounced temperature increases that can cause mechanical warpings of the measurement system, thereby producing measurement inaccuracies, for example via distortion of the beam fan relative to the detector, and/or can lead to increased mechanical wear, for example of a bearing.

Figure 4:
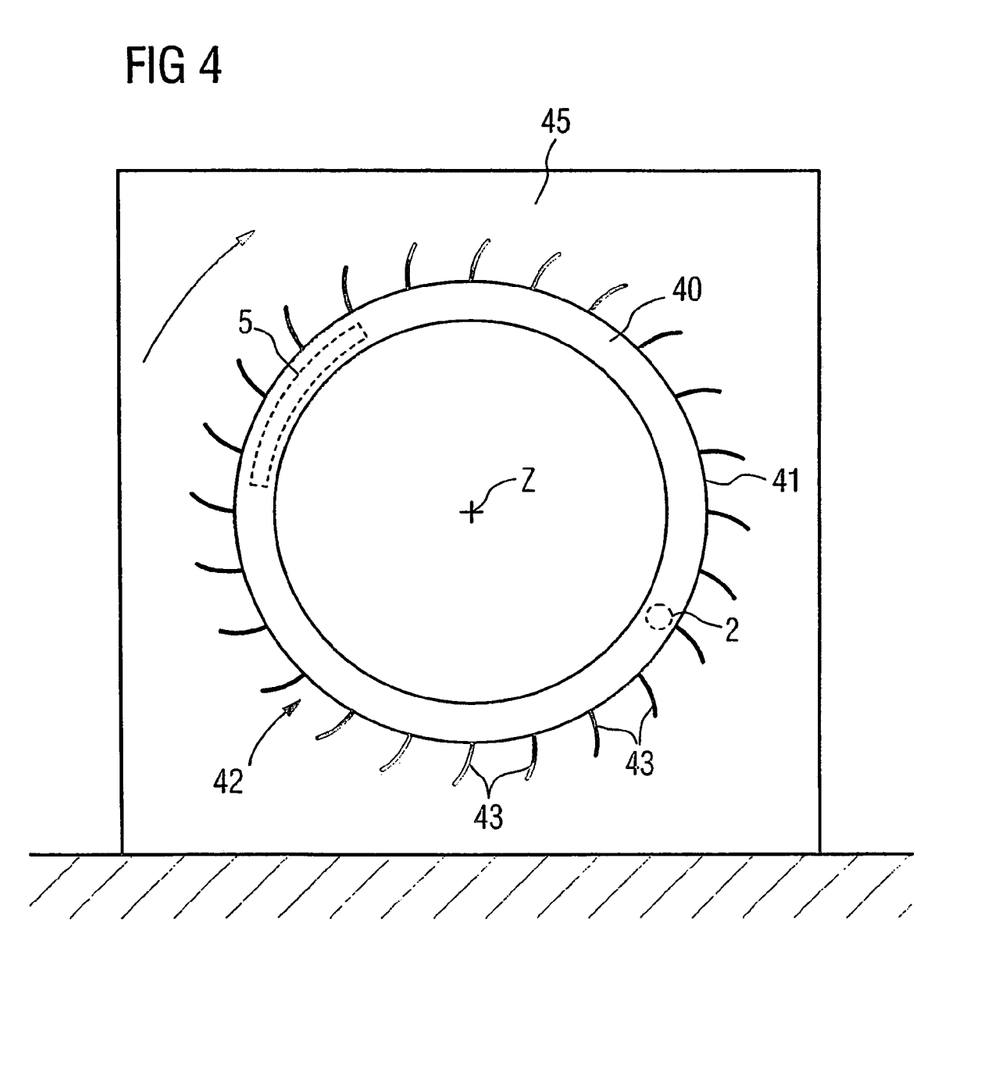
FIG. 4 illustrates cooling of a CT apparatus according to the invention.

A continuous rotation also allows the rotating measurement system to be shaped such that it is actively participating in the cooling, for example, by the mounting or the rotating frame 40 of the measurement system being designed so that it acts as an air mover. For this purpose—as shown schematically in FIG. 4—air scoops 43 can be present on the outside (front side or circumferential side) of a housing 41 of the rotating frame 40 as a part of a cooling device 42. The air current required for cooling during operation can then be generated without additional components. To prevent injuries, the air scoops 43 can be covered either by the frame 45 of the CT apparatus or by a special covering (mesh network etc.)

The invention can be applied in fields outside of medicine as well, for example in package inspection or in material examination.

Although modifications and changes may be suggested by those skilled in the art, it is the invention of the inventor to embody within the patent warranted heron all changes and modifications as reasonably and properly come within the scope of his contribution to the art.

I claim as my invention:

1. A method for operating a tomography apparatus comprising the steps of:
   positioning a first examination subject relative to a rotatable tomographic scanning unit;
   conducting a tomography examination of said first examination subject by rotating said scanning unit relative to said first examination subject to acquire tomography data from the first examination subject, at a rotation frequency selected, dependent on a type of said examination of said first examination subject, from among a plurality of different rotation frequencies;
   removing said first examination subject from said scanning unit and positioning a second examination subject relative to said scanning unit;
   conducting a tomography examination of said second examination subject by rotating said scanning unit relative to said second examination subject, to acquire tomography data from the second examination subject, at a rotation frequency, selected, dependent on a type of said examination of said second subject, from among said plurality of rotation frequencies; and
   rotating said scanning unit without interruption from a beginning of said examination of said first examination subject through an end of said examination of said second examination subject and, when neither of said first or second examination subjects is positioned relative to said scanning unit, rotating said scanning unit at a rest frequency selected from the group consisting of a rotation frequency that is smaller than a smallest of said plurality of rotation frequencies, and a rotation frequency that is an average of said plurality of rotation frequencies.

2. A method as claimed in claim 1 comprising selecting said rotation frequency, for each of said first examination subject and said second examination subject, from among a rotation frequency suitable for obtaining computed tomography data from a heart, and a rotation frequency suitable for obtaining computed tomography data from an abdomen.

3. A method as claimed in claim 1 comprising a time span for said uninterrupted rotation of said scanning unit from the group of time spans comprising a work shift, a work day and more than two examinations.

4. A method as claimed in claim 1 comprising employing an x-ray scanning unit as said scanning unit, having an x-ray source and an x-ray radiation detector that are rotatable around a system axis.

5. A method as claimed in claim 4 wherein at least one of said examination of said first examination subject or said examination of said second examination subject comprises:
   acquiring an x-ray shadow image of the examination subject while rotating said x-ray source around said examination subject;
   conducting a scan of the subject, selected from the group consisting of a slice scan and a volume scan, while rotating said x-ray source around said subject and emitting x-rays from said x-ray source at a plurality of angled positions relative to said system axis, to obtain a plurality of projection data sets respectively at said angle position from x-ray radiation detected by said detector system; and
   rotating said x-ray source around said examination subject without interruption from a beginning of acquisition of said x-ray shadow image through an end of said scan.

6. A method as claimed in claim 5 comprising conducting said scan as a spiral scan.

7. A method as claimed in claim 6 wherein the step of acquiring an x-ray shadow image of the examination subject comprises:
operating said x-ray source to emit said x-rays in a pulsed manner at an angled position that is predetermined for said x-ray shadow image, and acquiring radiographic data with said x-ray radiation detector; and
moving said x-ray source substantially parallel to said system axis and relative to said examination subject while emitting said x-rays in said pulsed manner.

8. A method as claimed in claim 4 wherein at least one of said examination of said first examination subject or said examination of said second examination subject comprises:
conducting a scan, selected from the group consisting of a slice scan and a volume scan, of the examination subject while emitting x-rays from said x-ray source while rotating said x-ray source through a plurality of angle positions around the examination subject, and acquiring respective data sets with the detector system at said angle positions, and while moving said x-ray source substantially parallel to said system axis and relative to said examination subject; and
generating an x-ray shadow image of the examination subject simultaneously with said scan by selecting projection data for said x-ray shadow image from the projection data sets that accumulate during said scan.

9. A method as claimed in claim 4 wherein at least one of said examination of said first examination subject or said examination of said second examination subject comprises:
conducting a scan, selected from the group consisting of a slice scan and a volume scan, of the examination subject while emitting x-rays from said x-ray source while rotating said x-ray source through a plurality of angle positions around the examination subject, and acquiring respective data sets with the detector system at said angle positions, and while moving said x-ray source substantially parallel to said system axis and relative to said examination subject; and
reconstructing a 3D data set from said projection data sets; and
from said 3D data set, electronically calculating an x-ray shadow image of the examination subject as a synthetic projection image.

10. A method as claimed in claim 1 comprising calibrating said tomography apparatus during rotation of said scanning unit.

11. A tomography apparatus comprising:
a rotatable scanning unit for acquiring tomographic data;
a bearing device for positioning a first examination subject relative to said scanning unit and for subsequently removing said first examination subject from said scanning unit and positioning a second examination subject relative to said scanning unit;
a control unit for operating said scanning unit to conduct a tomography examination of said first examination subject by rotating said scanning unit relative to said first examination subject to acquire tomography data from the first examination subject, at a rotation frequency selected, dependent on a type of said examination of said first examination subject, from among a plurality of different rotation frequencies, and to conduct a tomography examination of said second examination subject by rotating said scanning unit relative to said second examination subject to acquire tomography data from the second examination subject, at a rotation frequency, selected, dependent on a type of said examination of said second subject, from among said plurality of rotation frequencies, while rotating said scanning unit without interruption from a beginning of said examination of said first examination subject through an end of said examination of said second examination subject and, when neither of said first or second examination subjects is positioned relative to said scanning unit, rotating said scanning unit at a rest frequency selected from the group consisting of a rotation frequency that is smaller than a smallest of said plurality of rotation frequencies, and a rotation frequency that is an average of said plurality of rotation frequencies.

12. A tomographic apparatus as claimed in claim 11 wherein said control unit conducts at least one of said examination of said first examination subject or said examination of said second examination subject by acquiring an x-ray shadow image of the examination subject while rotating said x-ray source around said examination subject, conducting a scan of the subject, selected from the group consisting of a slice scan and a volume scan, while rotating said x-ray source around said subject and emitting x-rays from said x-ray source at a plurality of angled positions relative to said system axis, to obtain a plurality of projection data sets respectively at said angle position from x-ray radiation detected by said detector system, and rotating said x-ray source around said examination subject without interruption from a beginning of acquisition of said x-ray shadow image through an end of said scan.

13. A tomography apparatus as claimed in claim 11 wherein said scanning unit comprises a rotating frame with a cooling device mounted thereon, said cooling device comprising air drivers for generating an air current of a magnitude sufficient to cool said scanning unit during rotation of said rotating frame.

14. A tomography apparatus as claimed in claim 11 wherein said air drivers are air scoops.

15. A tomography apparatus as claimed in claim 11 wherein said rotating frame has an exterior, and wherein said air drivers are mounted at said exterior of said rotating frame.

* * * * *